(12) United States Patent
Meyer et al.

(10) Patent No.: US 7,442,175 B2
(45) Date of Patent: Oct. 28, 2008

(54) COMPRESSION SLEEVE HAVING AIR CONDUIT

(75) Inventors: Ann Meyer, Shrewsbury, MA (US); Garth Baker, North Easton, MA (US); Mark Vess, Hanson, MA (US); Malcolm G. Bock, Medfield, MA (US); Richard Braga, Taunton, MA (US); Jesse Denson, Lincoln, RI (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/299,488

(22) Filed: Dec. 12, 2005

(65) Prior Publication Data

US 2007/0135742 A1 Jun. 14, 2007

(51) Int. Cl.
*A61H 7/00* (2006.01)

(52) U.S. Cl. ........................ 601/151; 601/152

(58) Field of Classification Search ............... 601/15, 601/148–152; 602/13; 128/DIG. 15, DIG. 20
See application file for complete search history.

(56) References Cited

U.S. PATENT DOCUMENTS

| | | | |
|---|---|---|---|
| 2,533,504 A | 12/1950 | Poor | |
| 3,899,210 A * | 8/1975 | Samhammer et al. | 297/448.2 |
| 3,906,937 A | 9/1975 | Aronson | |
| 4,198,961 A | 4/1980 | Arkans | |
| 4,202,325 A | 5/1980 | Villari et al. | |
| 4,351,872 A | 9/1982 | Brosseau et al. | |
| 4,372,297 A * | 2/1983 | Perlin | 601/151 |
| 4,375,217 A | 3/1983 | Arkans | |
| 4,402,312 A * | 9/1983 | Villari et al. | 601/152 |
| 4,597,384 A | 7/1986 | Whitney | |
| 4,650,452 A | 3/1987 | Jensen | |
| 4,657,003 A | 4/1987 | Wirtz | |
| 4,682,588 A | 7/1987 | Curlee | |
| 4,762,121 A | 8/1988 | Shienfeld | |
| 4,773,397 A | 9/1988 | Wright et al. | |
| 4,827,912 A | 5/1989 | Carrington et al. | |
| 4,836,691 A | 6/1989 | Suzuki et al. | |
| 4,846,160 A | 7/1989 | Gardner et al. | |
| 4,846,189 A | 7/1989 | Sun | |
| 4,869,265 A | 9/1989 | McEwen | |
| 4,898,160 A | 2/1990 | Brownlee | |
| 4,938,226 A | 7/1990 | Danielsson | |
| 4,979,953 A | 12/1990 | Spence | |

(Continued)

FOREIGN PATENT DOCUMENTS

EP     0 303 029 A1     2/1989

(Continued)

OTHER PUBLICATIONS

Extended European Search Report in Application No. 06025443.0-1257, dated Sep. 5, 2007, 9 pages.

(Continued)

*Primary Examiner*—Michael A. Brown
(74) *Attorney, Agent, or Firm*—Edward S. Jarmolowicz

(57) ABSTRACT

A compression sleeve is described as having a first sheet, a second sheet attached to said first sheet and defining at least one inflatable section, and at least one conduit disposed in the at least one of said inflatable sections.

30 Claims, 6 Drawing Sheets

U.S. PATENT DOCUMENTS

| | | | |
|---|---|---|---|
| 5,048,536 A | 9/1991 | McEwen | |
| 5,117,812 A | 6/1992 | McWhorter | |
| 5,168,576 A | 12/1992 | Krent et al. | |
| 5,181,522 A | 1/1993 | McEwen | |
| 5,193,549 A | 3/1993 | Bellin et al. | |
| 5,211,162 A | 5/1993 | Gillen, Jr. et al. | |
| 5,226,564 A | 7/1993 | Steer et al. | |
| 5,383,919 A * | 1/1995 | Kelly et al. | 607/104 |
| 5,413,582 A | 5/1995 | Eaton | |
| 5,419,757 A | 5/1995 | Daneshvar | |
| 5,437,595 A | 8/1995 | Smith | |
| 5,578,055 A | 11/1996 | McEwen | |
| 5,591,200 A | 1/1997 | Cone et al. | |
| 5,626,556 A * | 5/1997 | Tobler et al. | 601/151 |
| 5,725,485 A | 3/1998 | Ribando et al. | |
| 5,741,295 A | 4/1998 | McEwen | |
| 5,772,830 A | 6/1998 | Lynn et al. | |
| 5,790,998 A * | 8/1998 | Crescimbeni | 5/648 |
| 5,795,312 A | 8/1998 | Dye | |
| 5,797,851 A | 8/1998 | Byrd | |
| 5,891,065 A | 4/1999 | Cariapa | |
| 5,931,797 A | 8/1999 | Tumey et al. | |
| 5,966,763 A | 10/1999 | Thomas et al. | |
| 5,968,072 A | 10/1999 | Hite et al. | |
| 5,976,300 A | 11/1999 | Buchanan et al. | |
| 6,001,119 A | 12/1999 | Hampson et al. | |
| 6,036,718 A | 3/2000 | Ledford et al. | |
| 6,051,016 A | 4/2000 | Mesaros et al. | |
| 6,080,120 A | 6/2000 | Sandman et al. | |
| 6,171,271 B1 | 1/2001 | Hornberg | |
| 6,203,510 B1 | 3/2001 | Takeuchi et al. | |
| 6,209,159 B1 | 4/2001 | Murphy | |
| 6,245,023 B1 | 6/2001 | Clemmons | |
| 6,273,866 B2 | 8/2001 | Thomas et al. | |
| 6,315,745 B1 | 11/2001 | Kloecker | |
| 6,385,864 B1 | 5/2002 | Sell, Jr. et al. | |
| 6,436,064 B1 | 8/2002 | Kloecker | |
| 6,447,467 B1 | 9/2002 | Barak | |
| 6,478,757 B1 | 11/2002 | Barak | |
| 6,488,643 B1 | 12/2002 | Tumey et al. | |
| 6,494,852 B1 | 12/2002 | Barak et al. | |
| 6,527,727 B2 | 3/2003 | Itonaga et al. | |
| 6,551,280 B1 | 4/2003 | Knighton et al. | |
| 6,589,267 B1 | 7/2003 | Hui | |
| 6,682,547 B2 | 1/2004 | McEwen et al. | |
| 6,852,089 B2 | 2/2005 | Kloecker et al. | |
| 6,860,862 B2 | 3/2005 | Waldridge et al. | |
| 6,862,989 B2 | 3/2005 | Belanger et al. | |
| 6,866,636 B2 | 3/2005 | Inoue et al. | |
| 2002/0169399 A1 | 11/2002 | Rastegar et al. | |
| 2003/0199922 A1 | 10/2003 | Buckman | |
| 2003/0205156 A1 | 11/2003 | Belanger et al. | |
| 2004/0068290 A1 | 4/2004 | Bates et al. | |
| 2004/0158285 A1 | 8/2004 | Pillai | |
| 2004/0181254 A1 | 9/2004 | Choi et al. | |

FOREIGN PATENT DOCUMENTS

| | | |
|---|---|---|
| EP | 0 392 669 A2 | 10/1990 |
| EP | 0 408 049 B1 | 9/1995 |
| EP | 1 468 816 A1 | 10/2004 |
| GB | 2 178 663 A | 2/1987 |
| GB | 2 183 483 A | 6/1987 |
| GB | 2 373 444 A | 9/2002 |
| WO | WO 98 30133 A1 | 7/1998 |
| WO | 9930607 | 6/1999 |

OTHER PUBLICATIONS

Jonathan S. Mittelman, MD; Effectiveness of Leg Compression in Preventing Venous Stasis, The American Journal of Surgery, Dec. 1982, p. 611-613, vol. 144, No. 6, Elsevier Publ., Bridgewater, NJ, USA.

* cited by examiner

COMPRESSION SLEEVE HAVING AIR CONDUIT

BACKGROUND

1. Technical Field

The present disclosure relates generally to a compression sleeve for use in a system for applying compressive forces or pressure to a patient's limb, such as the leg. In particular, the present disclosure relates to a compression sleeve that maintains air flow in the entire sleeve during compression therapy when wrapped around the limb of an individual.

2. Description of Related Art

Compression devices for applying compressive forces to a selected area of a person's anatomy are generally employed to improve blood flow in the selected area. Compression devices that provide intermittent pulses of a compressed fluid (e.g. air) to inflate at least one inflatable chamber in a sleeve are particularly useful. This cyclic application of pressure provides a non-invasive method of prophylaxis to reduce the incidence of deep vein thrombosis (DVT), and the like. These compression devices find particular use during surgery on patients with high-risk conditions such as obesity, advanced age, malignancy, or prior thromboembolism. Patients who have this condition often have swelling (i.e. edema) and tissue breakdown (i.e. venous stasis ulcer) in the lower leg.

In general, compression devices include a sleeve having at least one fluid inflatable pressure chamber progressively arranged longitudinally along the sleeve. A pressure source (e.g. a pump) is provided for intermittently forming a pressure pulse within these inflatable chambers from a source of pressurized fluid during periodic compression cycles. The compression sleeves provide a pressure gradient along the patient's limbs during these compression cycles, which progressively decreases from the lower portion to the upper portion of the limb (i.e. from the ankle to the thigh).

Examples of compression sleeves are disclosed in U.S. Pat. Nos. 4,013,069 and 4,030,488 to Hasty, U.S. Pat. Nos. 4,029,087 and 5,795,312 to Dye, and U.S. Pat. No. 5,626,556 to Tobler et al., all of which are currently owned by Tyco Healthcare Group, LP and are incorporated by reference herein in their entirety. Other examples of compression sleeves are disclosed in U.S. Pat. No. 4,696,289 to Gardner et al. and U.S. Pat. No. 5,989,204 to Lina.

When compression therapy is administered to a patient, the inflatable pressure chambers of the compression sleeves of the foregoing description may include trapped air. Trapped air changes the volume of a chamber, thus reducing the pressure gradient along the patient's limb during treatment. The shape, weight, and position of a patient's limb will contribute to the size and number of pockets of air formed. An example of compression treatment method is disclosed in U.S. Pat. No. 6,231,532 to Watson et al., which is currently owned by Tyco Healthcare Group, LP, the contents of which are hereby incorporated by reference herein in their entirety.

SUMMARY

The present disclosure is directed towards a compression sleeve for applying compressive forces or pressure to a selected portion of a patient's anatomy. The compression sleeve includes a sleeve having a plurality of inflatable sections and at least one conduit disposed within one of the plurality of inflatable sections. A plurality of lumens is provided for operatively connecting the sleeve to a controller having a source of pressurized fluid (e.g. air). The compression sleeve further includes hook and loop features attached thereto for securing the compression sleeve to the selected portion of the patient's anatomy.

In one embodiment, the compression sleeve includes a sleeve for applying compressive forces or pressure to a patient's limb (e.g. a leg). The sleeve includes first and second sheets defining a plurality of inflatable sections or chambers, and at least one air conduit disposed within the plurality of inflatable sections. The first and second sheets are fixedly joined by radio frequency (RF) welding, or by other suitable methods, along their corresponding perimeters, thereby defining a plurality of inflatable sections therebetween. The second layer provides the attachment surface for the hook and loop features.

The plurality of inflatable sections is configured for receiving and retaining a pressurized fluid (e.g. air) from a pressurized fluid source for exerting compressive forces or pressure to a portion of the patient's leg during successive pressure applying cycles.

The air conduit is configured and adapted for creating a passage for facilitating the flow of the pressurized air in the plurality of inflatable sections or chambers during compression therapy. When the pressurized air is introduced into each inflatable section, the passage created by the air conduit between the first and second sheets improves the inflation characteristics of each inflatable section. Moreover, the air conduit, during deflation of the compression sleeve, channels the pressurized air towards the fluid source, thereby improving the removal of the pressurized air and minimizing the formation of random pockets, of pressurized air.

Other features of the presently disclosed compression sleeve will become apparent from the following detailed description, taken in conjunction with the accompanying drawings that illustrate, by way of example, the presently disclosed compression sleeve.

BRIEF DESCRIPTION OF THE DRAWINGS

The features of the presently disclosed compression sleeve will become more readily apparent by referring to the following detailed description of embodiments, which are described hereinbelow with reference to the drawings, wherein:

FIGS. 2A-2B are plan and cross-sectional views, respectively, of a first embodiment of an air conduit in accordance with the present disclosure;

FIGS. 3A-3B are plan and cross-sectional views, respectively, of a second embodiment of the air conduit in accordance with the preset disclosure;

FIGS. 4A-4B are plan and cross-sectional views, respectively, of yet another embodiment of the air conduit in accordance with the preset disclosure;

FIGS. 5A-5B are plan and cross-sectional views, respectively, of yet another embodiment of the air conduit in accordance with the preset disclosure;

FIGS. 6A-6B are plan and cross-sectional views, respectively, of yet another embodiment of the air conduit in accordance with the preset disclosure;

FIGS. 7A-7B are plan and cross-sectional views, respectively, of yet another embodiment of the air conduit in accordance with the preset disclosure;

DETAILED DESCRIPTION

Figure 1:
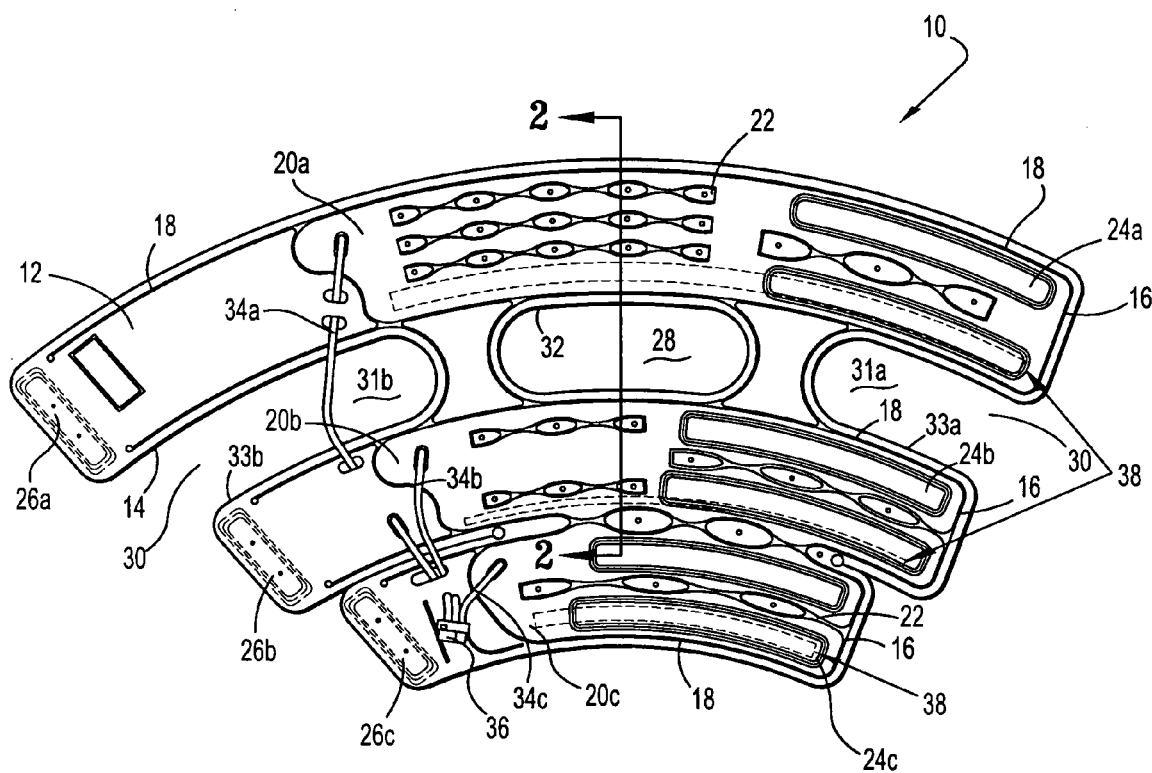
FIG. 1 is a plan view of a compression sleeve, in accordance with the present disclosure.

Referring now to the drawing figures, in which like reference numerals identify identical or corresponding elements, various embodiments of the presently disclosed compression sleeve will now be described in detail. The compression sleeve of the present disclosure is similar to the compression sleeve disclosed in U.S. Pat. No. 5,626,556 to Tobler et al. and U.S. Pat. No. 5,795,312 to Dye, both of which are currently owned by Tyco Healthcare Group, LP and are incorporated by reference herein in their entirety.

With initial reference to FIG. 1, a compression sleeve in accordance with the present disclosure is illustrated and is designated generally as compression sleeve 10. Compression sleeve 10 is adapted for use in a system for applying compressive forces or pressure to a portion of a patient's limbs such as, for example, the legs. Compression sleeve 10 includes first or outer sheet 12 and second or inner sheet 14 connected by a plurality of laterally extending sealing lines 16 and longitudinally extending sealing lines 18 connecting the ends of lateral sealing lines 16. First and second sheets 12, 14 are adapted as inner gas-impervious sheets, for placement against the person's limbs. Sealing lines 16, 18 may be formed by radio frequency (RF) welding, etc. Moreover, sealing lines 16, 18 define a plurality of longitudinally disposed inflatable sections or chambers 20a, 20b, and 20c which are capable of retaining a pressurized fluid such as, for example, air, in order to exert compressive forces to the patient's limbs during successive pressure-applying cycles.

First sheet 12 may, for example, comprise a suitable flexible polymeric material such as, for example, polyvinyl chloride (PVC) on the order of 5-10 mils thick. Second sheet 14 will preferably comprise a similar polymeric material (i.e. 5-10 mil PVC) having a non-woven material, such as polyester, laminated to the inner surface that is placed against the limb, thereby increasing the comfort of the wearer. Each inflatable section 20a, 20b, and 20c may include at least one wave-shaped border 22. When inflatable sections 20a, 20b, and 20c abut one another, wave-shaped border 22 defines a plurality of un-inflatable "eyes", as illustrated in FIG. 1.

In addition, compression sleeve 10 includes a plurality of hook and loop fasteners for attaching the sleeve about the patient's limb. Hook and loop fasteners include a set of spaced strips 24a, 24b, and 24c, such as loop material positioned on first sheet 12. Strips 24a, 24b, and 24c extend laterally at the inflatable sections 20a, 20b, and 20c, and cooperate with a set of spaced hook materials 26a, 26b, and 26c disposed on second sheet 14 for releasably fastening sleeve 10 to the leg.

When compression sleeve 10 is attached to the patient's limbs, each inflatable section 20a, 20b, and 20c is oriented in a direction that is substantially transverse to a longitudinal axis of the patient's limb. That is, compression sleeve 10 encircles the leg.

Compression sleeve 10 includes an elongated opening 28 extending through what would be the knee region 30 when the sleeve is employed to apply compressive forces or pressure to the limb, opening 28 being defined by peripheral edges 32 extending around the opening. In addition, the knee region 30 has elongated cut-outs or openings 31a and 31b being defined by peripheral side edges 33a and 33b, respectively. Compression sleeve 10 is provided with a set of lumens 34a, 34b and 34c having a connector 36 for operably connecting lumens 34a, 34b and 34c to a controller (not shown) having a source of pressurized fluid (e.g. air).

With continued reference to FIG. 1, compression sleeve 10 further includes a plurality of air conduits 38 disposed within at least one of inflatable sections 20a, 20b, or 20c. Air conduit 38 is adapted for creating a passage for facilitating the flow of the pressurized air in the at least one inflatable section 20a, 20b, or 20c when compression therapy is being administered. Each air conduit 38 facilitates the flow of the pressurized air within inflatable sections 20a, 20b, or 20c by separating first and second sheets 12 and 14 when compression sleeve 10 is in a deflated state. Although air conduit 38 is shown as a linear structure in the various figures, air conduit 38 may be shaped to follow an arc that substantially corresponds to the arc defined by inflatable sections 20a, 20b, or 20c (see FIG. 1). Air conduit 38 may be formed from extruded PVC. It is envisioned that each air conduit 38 may be constructed to fit the shape of other flexible sleeves and foot cuffs such as those available from Kendall's product catalog H-4693VT "Vascular Therapy Products."

In use, compression sleeve 10, in accordance with the present disclosure, is configured to apply compressive forces to a patient's leg. Compression sleeve 10 is positioned about the leg of a patient, wherein hook materials 26a, 26b, and 26c are configured for engaging loop materials 24a, 24b, and 24c. After placement of compression sleeve 10 about a leg of the patient and connecting compression sleeve 10 to pressurized fluid source via connector 36, the controller (not shown) may then be actuated for supplying pressurized air to compression sleeve 10 and initiating compression therapy. Thus, the controller intermittently inflates inflatable sections 20a, 20b, and 20c sequentially during periodic compression cycles and defines a pressure gradient profile.

Air conduit 38 inhibits the formation of random pockets of air in each of the inflatable sections. When the pressurized air is introduced into each inflatable section 20a, 20b, and 20c, the passage created by the at least one air conduit 38 located between first and second sheets 12, 14, improves the inflation characteristics of each inflatable section. In devices that do not include at least one air conduit 38, as inflatable sections 20a, 20b, or 20c deflate, first and second sheets 12, 14 collapse and may form random pockets of pressurized air. These pockets randomly redirect and/or restrict the flow of the pressurized fluid through the inflatable sections 20a, 20b, or 20c, thereby obstructing the removal of the pressurized fluid.

By positioning air conduit 38 within inflatable sections 20a, 20b, or 20c, a passage is created for facilitating the flow of pressurized fluid in each of the inflatable sections 20a, 20b, or 20c. Deflation between successive inflation cycles occurs by returning the air in inflatable sections 20a, 20b, and 20c to the controller or to another vent (not shown), as is known in the art. Air conduit 38 effectively channels the pressurized air towards lumen 34a, 34b, or 34c, thus minimizing the formation of random pockets of pressurized air in each inflatable section 20a, 20b, or 20c. In addition, air conduit 38 channels the pressurized air towards lumens 34a, 34b, or 34c thereby improving the removal rate of the pressurized air and minimizing the formation of random pockets of pressurized air throughout compression sleeve 10.

Figure 2C:
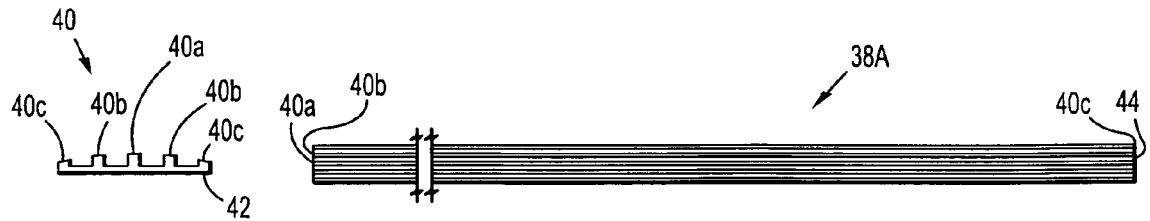
FIG. 2C is a cross-sectional view taken along line 2-2 in FIG. 1, illustrating the air conduit of FIG. 2A positioned within the inflatable sections of the compression sleeve.
Figure 2C:
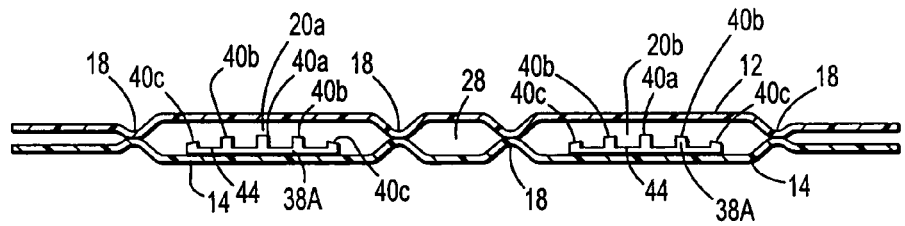

With reference to FIGS. 2A-2C, one embodiment of air conduit 38 is illustrated and is designated generally as air conduit 38A. Air conduit 38A includes a plurality of ridges or ribs 40 extruding upwards from a base member 42. Base member 42 is adhesively fastened to second sheet 14 or first sheet 12 of inflatable sections 20a, 20b, or 20c, and ribs 40 are in releasable contact with the first sheet 12 or second sheet 14 of the inflatable section 20a, as illustrated in FIG. 2C. The plurality of ribs 40 includes a center rib 40a, middle ribs, 40b, and outer ribs 40c that will be discussed in detail hereinbelow.

With particular reference to FIG. 2B, the height of ribs 40 is at a minimum at the outer edges of base member 42 and progressively increases towards the center of the base member 42 such that center rib 40a has the greatest height of ribs 40. Base member has a thickness from about 19 mils to about 39 mils. In one embodiment, center rib has a height from about 65 mils to about 85 mils, middle ribs 40b have a height from about 43 mils to about 63 mils, and outer ribs have a height from about 29 mils to about 49 mils. Further still, center rib has a width from about 50 mils to about 70 mils, while middle and outer ribs 40b and 40c have a width of about 40 mils to about 60 mils. Therefore, air conduit 38 has a low profile and, in combination with first and second sheets 12, 14, defines a low profile compression sleeve 10. Moreover, adjacent middle and outer ribs 40b and 40c, respectively, are spaced apart defining troughs 44 therebetween. Troughs 44 fluidly couple the opposing ends of air conduit 38A and are configured for channeling the pressurized air within inflatable sections 20a, 20b, or 20c towards lumens 34a, 34b, or 34c. In use, when the pressurized air is introduced into inflatable sections 20a, 20b, and 20c, the passage created by ribs 40 in air conduit 38A improves the inflation characteristics of inflatable sections 20a, 20b, or 20c. During deflation, troughs 44 channel the pressurized air towards lumens 34a, 34b, or 34c, effectively improving the removal of the pressurized air and minimizing the formation of random pockets of pressurized air.

Figure 3C:
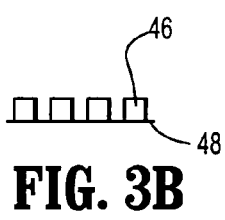
FIG. 3C is a cross-sectional view taken along line 2-2 in FIG. 1, illustrating the air conduit of FIG. 3A positioned within the inflatable sections of the compression sleeve.
Figure 3C:
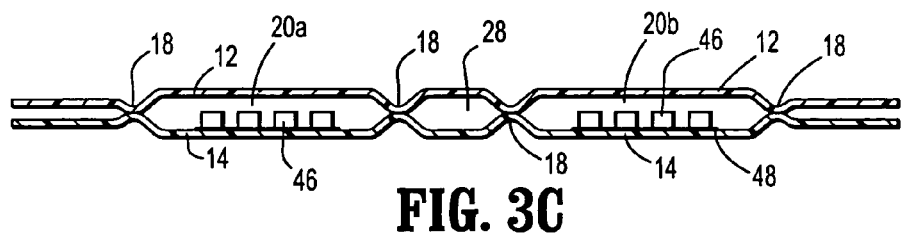

With reference to FIGS. 3A, 3B and 3C, a second embodiment of air conduit 38, in accordance with the present disclosure, is illustrated and is designated generally as air conduit 38B. As best illustrated in FIG. 3B, air conduit 38B includes a plurality of randomly placed cylindrical pins or knobs 46 extending upward from a base member 48. Base member 48 is fastened to second sheet 14 or first sheet 12 of inflatable sections 20a 20b, or 20c and cylindrical pins 46 are in releasable contact with first sheet 12 or second sheet 14 of at least one of inflatable sections 20a, 20b, or 20c, as illustrated in FIG. 3C. Thus, air conduit 38B effectively separates first and second sheets 12 and 14 when compression sleeve 10 is in a deflated state. The passage created by the plurality of cylindrical pins 46 improves the inflation characteristics of inflatable sections 20a, 20b, or 20c. During deflation, cylindrical pins 46 channel the pressurized air towards lumens 34a, 34b, or 34c, effectively improving the removal of the pressurized air and minimizing the formation of random pockets of pressurized air.

Figure 4C:
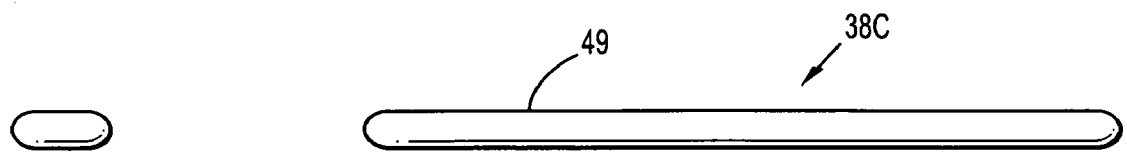
FIG. 4C is a cross-sectional view taken along line 2-2 in FIG. 1, illustrating the air conduit of FIG. 4A positioned within the inflatable sections of the compression sleeve.
Figure 4C:
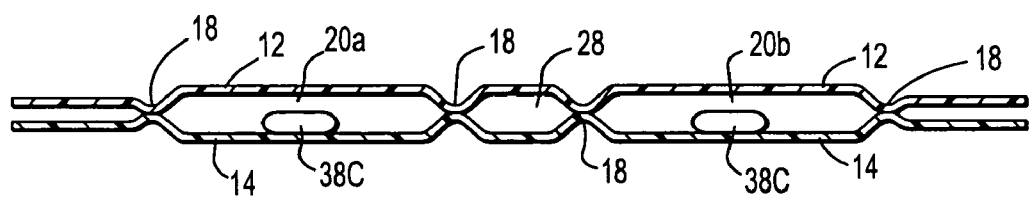

With reference to FIGS. 4A-4C, another embodiment of air conduit 38 is illustrated and is designated generally as air conduit 38C. Air conduit 38C includes at least one inflatable elongated sheath 49 positioned within at least one of inflatable sections 20a, 20b, or 20c. The at least one elongated sheath 49 is adhesively fastened to second sheet 14 or first sheet 12 and is in releasable contact with first sheet 12 or second sheet 14, as illustrated by FIG. 4C. In an alternative embodiment, the sheath may be RF welded to an inside surface of second sheet 14 or first sheet 12. In this particular embodiment, air conduit 38C forms a circumferential bubble passageway, as illustrated in FIG. 4C. The at least one elongated sheath 49 may be formed from a foam material wherein the foam material does not collapse under the load of the leg, thus maintaining a separation between first and second sheets 12 and 14. In use, when the pressurized air is introduced into inflatable sections 20a, 20b, and 20c, the circumferential bubble passageway formed by air conduit 38C improves the inflation characteristics of inflatable sections 20a, 20b, or 20c. During deflation, the at least one elongated sheath 49 channels the pressurized air towards lumens 34a, 34b, or 34c, effectively improving the removal of the pressurized air and minimizing the formation of random pockets of pressurized air. In addition, elongated sheath 49 may also be positioned on the outer surface of first and second sheets 12 and 14 for providing a rigid support structure of the sleeve for receiving the leg. Alternatively, a separate leg support may be provided to keep the limb raised off the bed surface.

Figure 5C:
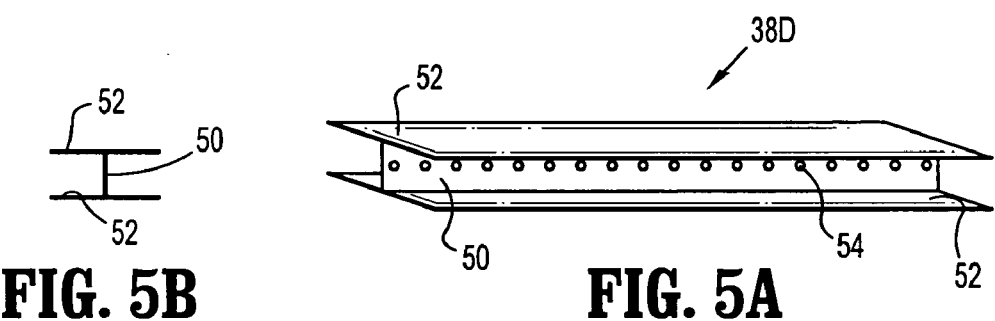
FIG. 5C is a cross-sectional view taken along line 2-2 in FIG. 1, illustrating the air conduit of FIG. 5A positioned within the inflatable sections of the compression sleeve.
Figure 5C:
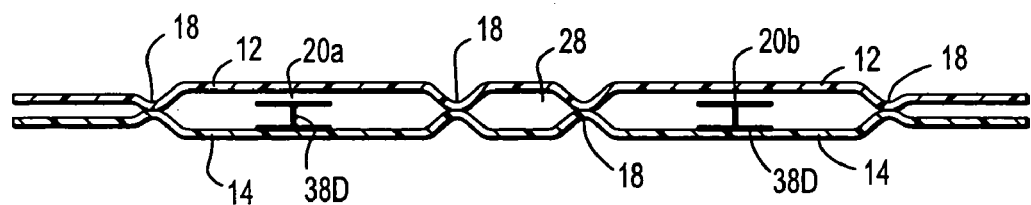

With reference to FIGS. 5A, 5B and 5C, yet another embodiment of air conduit 38 is illustrated and is designated generally as air conduit 38D. Air conduit 38D is similar to air conduit 38A and will only be discussed in detail to the extent necessary to identify differences in construction and operation. Air conduit 38D includes a semi-rigid "I" beam having a web 50 and two flange portions 52 disposed on either end of web 50. Air conduit 38D is positioned within at least one of inflatable sections 20a, 20b, or 20c in a manner illustrated in FIG. 5C for separating first and second sheets 12 and 14, thus preventing sleeve 10 from collapsing under the weight of the patient's leg. In addition, a plurality of openings 54 is disposed on web 50 for facilitating communication throughout inflatable sections 20a, 20b, or 20c. In use, when the pressurized air is introduced into inflatable sections 20a, 20b, or 20c, the plurality of openings 54 disposed on web 50 improves the inflation characteristics of inflatable sections 20a, 20b, or 20c. During deflation, the semi-rigid "I" beam of air conduit 38D channels the pressurized air towards lumens 34a, 34b, or 34c, effectively improving the removal of the pressurized air and minimizing the formation of random pockets of pressurized air.

Figure 6C:
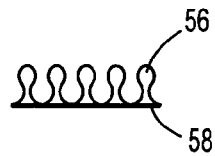
FIG. 6C is a cross-sectional view taken along line 2-2 in FIG. 1, illustrating the air conduit of FIG. 6A positioned within the inflatable sections of the compression sleeve.
Figure 6C:
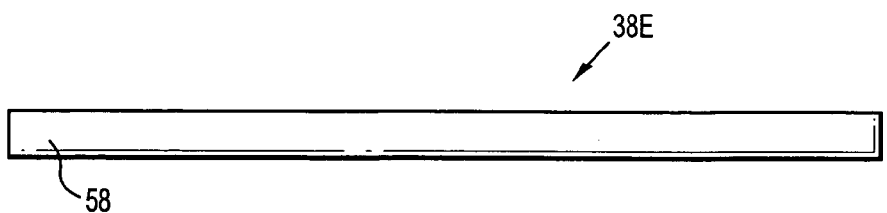
Figure 6C:
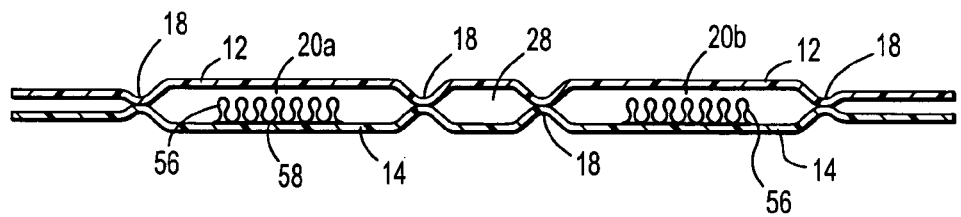

With reference to FIGS. 6A-6C, yet another embodiment of air conduit 38 is illustrated and is designated generally as air conduit 38E. Air conduit 38E is similar to air conduit 38A and will only be discussed in detail to the extent necessary to identify differences in construction and operation. Air conduit 38E includes a plurality of longitudinal corrugated extrusions 56 attached to base 58. Corrugated extrusions 56 form a passageway for air to pass therethrough. It is envisioned that corrugated extrusions 56 will permit air to infiltrate into inflatable sections 20a, 20b, or 20c. In use, when the pressurized air is introduced into inflatable sections 20a, 20b and 20c, the corrugated extrusions 56 improves the inflation characteristics of inflatable sections 20a, 20b, or 20c. During deflation, the corrugated extrusions channel the pressurized air towards lumens 34a, 34b, or 34c, effectively improving the removal of the pressurized air and minimizing the formation of random pockets of pressurized air.

Figure 7C:
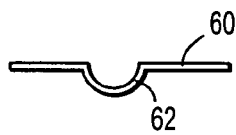
FIG. 7C is a cross-sectional view taken along line 2-2 in FIG. 1, illustrating the air conduit of FIG. 7A positioned within the inflatable sections of the compression sleeve.
Figure 7C:
Figure 7C:
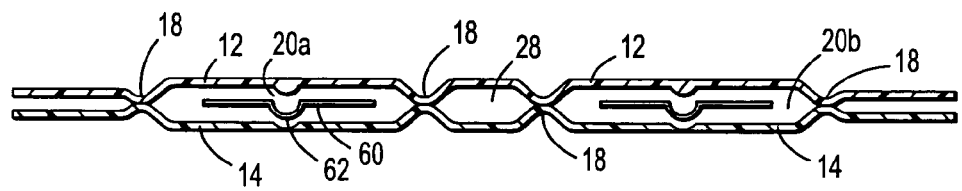

With reference to FIGS. 7A-7C, yet another embodiment of air conduit 38 is illustrated and is designated generally as air conduit 38F. Air conduit 38F is similar to air conduit 38A and will only be discussed in detail to the extent necessary to identify differences in construction and operation. Air conduit 38F includes a base portion 60 having a central longitudinal channel 62, as illustrated in FIG. 7B. In this particular embodiment, air conduit 38F is installed within inflatable sections 20a, 20b, or 20c such that channel 62 forms a passageway therethrough. Base portion 60 and channel 62 may be inflatable or, alternatively, may be RF welded onto first and second sheets 12, 14. They may also be reinforced with an additional layer of PVC sheet to form a more rigid conduit. In use, when the pressurized air is introduced into inflatable sections 20a, 20b, and 20c, central longitudinal channel 62 improves the inflation characteristics of inflatable sections 20a, 20b, or 20c. During deflation, longitudinal channel 62 directs the pressurized air towards lumens 34a, 34b, or 34c, effectively improving the removal of the pressurized air and minimizing the formation of random pockets of pressurized air.

Figure 7D:
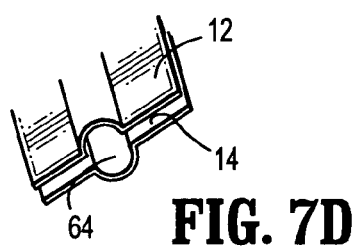
FIG. 7D is a front elevational view of the compressive sleeve showing a linear void across the sleeve.

Alternatively, first and second sheets 12, 14 may be RF welded, having a pre-fabricated feature, wherein a linear void 64 across the sleeve is formed, as illustrated in FIG. 7D. In this particular embodiment, linear void 64 directs the pressurized air towards lumen 34a, 34b, and 34c for improving the removal of the pressurized air and minimizing the formation of random pockets of pressurized air.

Figure 8B:
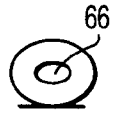
FIGS. 8A-8B are plan and cross-sectional views, respectively, of yet another embodiment of the air conduit in accordance with the preset disclosure.
Figure 8A:
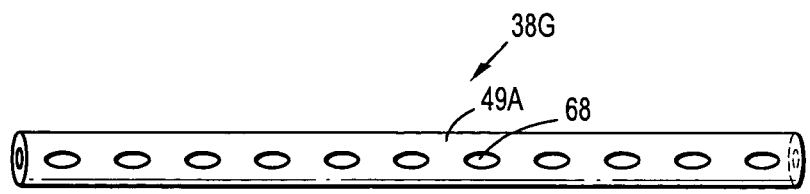
Figure 8C:
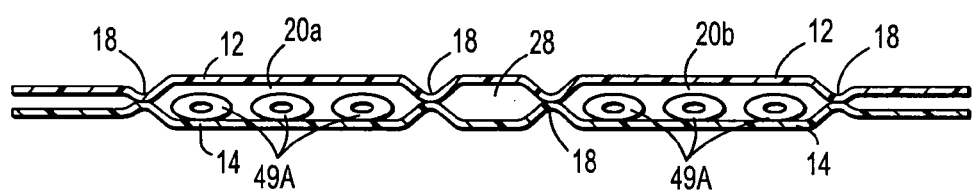
FIG. 8C is a cross-sectional view taken along line 2-2 in FIG. 1, illustrating the air conduit of FIG. 8A positioned within the inflatable sections of the compression sleeve.

With reference to FIGS. 8A, 8B and 8C, yet another embodiment of air conduit 38 is illustrated and is designated generally as air conduit 38G. Air conduit 38G is similar to air conduit 38C (FIGS. 4A, 4B and 4C) and will only be discussed in detail to the extent necessary to identify differences in construction and operation. Air conduit 38G includes at least one elongated sheath 49A having an axial aperture 66 (FIG. 8B) and a plurality of transverse openings 68 (FIG. 8A). Axial aperture 66 and transverse openings 68 permit air to disperse across the full length of compression sleeve 10. The at least one elongated sheath 49A may be positioned within inflatable sections 20a, 20b, or 20c, adhesively fastened to second sheet 14 or the first sheet 12 and in releasable contact with first sheet 12 or second sheet 14, as illustrated in FIG. 8C. In use, when the pressurized air is introduced into inflatable sections 20a, 20b, and 20c, axial aperture 66 and transverse openings 68 of the at least one elongated sheath 49A improves the inflation characteristics of inflatable sections 20a, 20b, or 20c. During deflation, axial aperture 66 channels the pressurized air towards lumens 34a, 34b, or 34c, effectively improving the removal of the pressurized air and minimizing the formation of random pockets of pressurized air.

Figure 9:
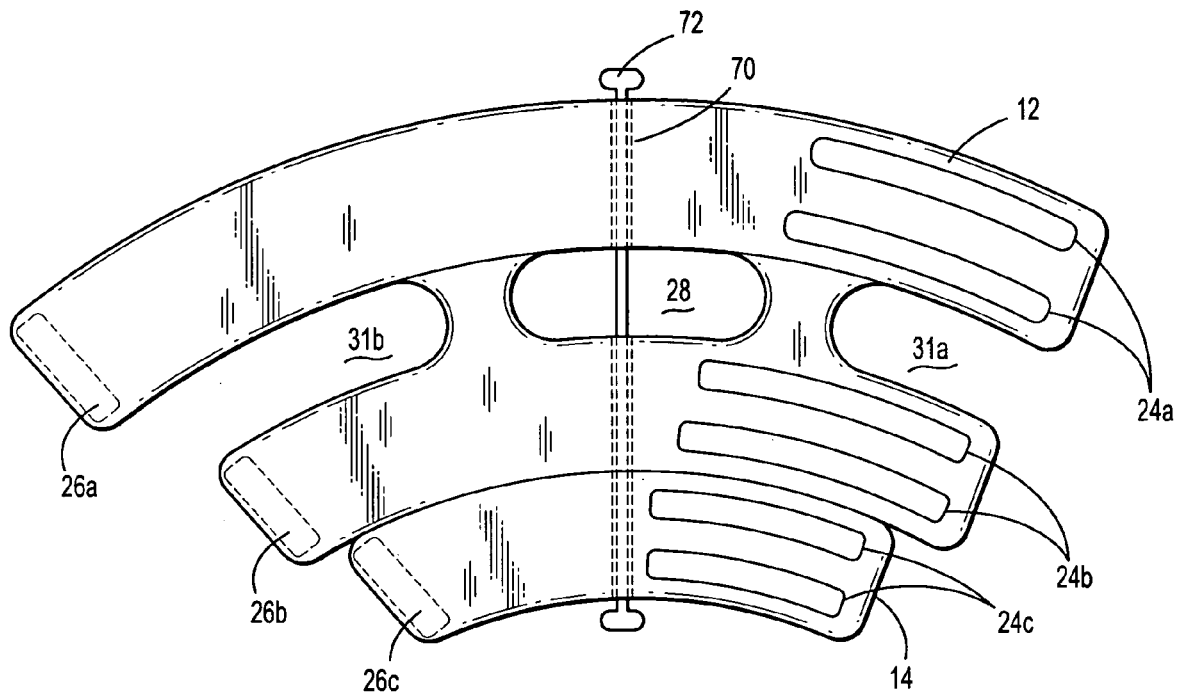
FIG. 9 is a plan view of the compression sleeve illustrating yet another embodiment of the air conduit in accordance with the present disclosure.

Other methods of facilitating the flow of pressurized air within inflatable sections 20a, 20b, and 20c are envisioned. For example, compression sleeve 10 may be manufactured to include a channel 70 for sliding a support member 72 therethrough, as illustrated in FIG. 9, for providing a rigid support structure to compression sleeve 10. Thus, support member 72 will rigidly support the weight of the leg. Alternatively, sealing lines 16 (FIG. 1) may be strategically placed along first and second sheets 12, 14 for facilitating the passage of air. Moreover, inflatable sections 20a, 20b, and 20c may be filled with styrene foam pellets for adding structural rigidity and still permitting the flow of pressurized air throughout inflatable sections 20a, 20b, and 20c. In addition, a plurality of connectors 36 may be strategically installed throughout the compression sleeve for supplying inflatable sections 20a, 20b, and 20c with pressurized air from a plurality of points. Likewise, the plurality of connectors 36 can be actuated to deflate a chamber to minimize air pockets. Moreover, the strength of the sleeve material may be increased in order to allow for increased burst strength, permitting more pressure and volume to raise the large limb. For example, first and second sheets 12, 14 may be formed from a rigid material to prevent inflatable sections 20a, 20b, and 20c from collapsing under the weight of a large limb. Moreover, during manufacture of compression sleeve 10, a plurality of passageways may be embossed along the surface of first and second sheets 12, 14.

Figure 10A:
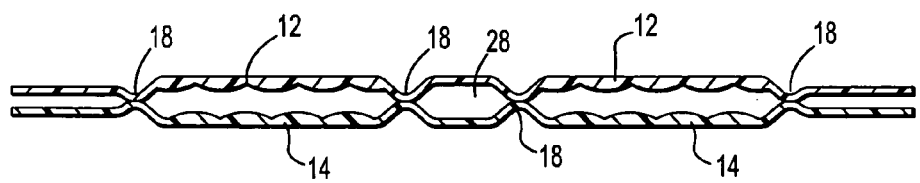
FIGS. 10A-B are cross-sectional views of another embodiment of the compression sleeve illustrating various textures of an inner surface of first and second sheets in accordance with the present disclosure.
Figure 10B:
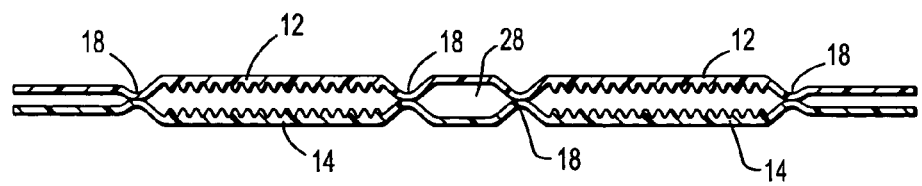

With reference to FIGS. 10A and 10B, first and second sheets 12, 14 may include a design or feature wherein the texture of the sleeve improves the flow of air. For example, particular textures may be provided on an inside surface of first and second sheets 12, 14, as shown in FIGS. 10A and 10B, such that they never collapse fully, thus facilitating the passage of the pressurized air. The texture may be laminated or may form part of first and second sheets 12 and 14. In use, when the pressurized air is introduced into inflatable sections 20a, 20b, and 20c, the texture on the inside surface of first and second sheets 12 and 14 improves the inflation characteristics of inflatable sections 20a, 20b, and 20c. During deflation, the textures on the inside surface of first and second sheets 12 and 14 assist in channeling the pressurized air towards lumens 34a, 34b, and 34c, effectively improving the removal of the pressurized air and minimizing the formation of random pockets of pressurized air. One skilled in the art will recognize other fluids besides air can be used without departing from the scope of the invention.

It will be understood that numerous modifications and changes in form and detail may be made to the embodiments of the present disclosure. For example, it is contemplated that numerous other configurations of the conduit may be used, and the material of the sleeve and/or conduit may be selected from numerous materials, other than those specifically disclosed. Therefore, the above description should not be construed as limiting, but merely as exemplifications of the various embodiments.

What is claimed is:

1. A compression sleeve, comprising:
    a first sheet;
    a second sheet attached to said first sheet and defining at least one inflatable section having dimensions in directions generally parallel to the first and second sheets; and
    at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a base member and a plurality of ridges attached to a first surface of the base member.

2. The compression sleeve as recited in claim 1, further comprising:
    a connector for connecting the lumen to a source of pressurized fluid; and
    a plurality of fasteners comprising hook and loop fastener components adapted for securing the sleeve about a portion of a patient's body.

3. The compression sleeve as recited in claim 1, wherein the at least one conduit is fastened to one of the first or second sheets.

4. The compression sleeve as recited in claim 1, wherein the height of the plurality of ridges is at a minimum at an outer edge of the base member and at a maximum at a central portion of the base.

5. The compression sleeve as recited in claim 1, wherein adjacent ridges are spaced apart defining a trough therebetween.

6. The compression sleeve as recited in claim 1, wherein the at least one conduit is formed from a polyvinyl chloride.

7. The compression sleeve as recited in claim 1, wherein the at least one conduit includes a base member defining a central longitudinal channel therethrough.

8. The compression sleeve as recited in claim 1, wherein the at least one conduit includes a plurality of longitudinal tubes.

9. A compression sleeve as recited in claim 1, wherein the first and second sheet is sealed along a sealing line for providing a chamber capable of withstanding a pressure from a fluid without leaking.

10. A compression sleeve as recited in claim 9, wherein the sealing line formation is selected from a group comprising: heat, RF welding, stitching, sewing, solvent bonding, stapling and stamping.

11. A compression sleeve as recited in claim 1, wherein at least one air tube is connected to the inflatable section for inflating and deflating the inflatable section thereby providing compression therapy.

12. A compression sleeve as recited in claim 1, wherein the at least one conduit is formed at the perimeter of the inflatable section.

13. A compression sleeve as recited in claim 1, wherein the conduit minimizes the formation of trapped fluid in the inflatable section.

14. A compression sleeve, comprising:
a first sheet;
a second sheet attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a base member and a plurality of pins attached to a first surface of the base member.

15. A compression sleeve, comprising:
a first sheet;
a second shoot attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes an inflatable elongated sheath, and further wherein the elongated sheath is formed from semi-rigid foam.

16. A compression sleeve, comprising:
a first sheet;
a second sheet attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle wherein at least one conduit includes an inflatable elongated sheath, and further wherein the elongated sheath includes a plurality of openings transversely positioned therethrough.

17. A compression sleeve, comprising:
a first sheet;
a second sheet attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a beam having a web portion and two flange portions disposed on both ends of the web portion.

18. The compression sleeve as recited in claim 17, wherein the web portion includes a plurality of openings.

19. A compression sleeve, comprising:
a first sheet;
a second sheet attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a plurality of longitudinal corrugated extrusions.

20. A compression sleeve, comprising:
a first sheet;
a second sheet attached to said first sheet and defining at least one inflatable section having dimensions in directions generally parallel to the first and second sheets; and
at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a plurality of styrene foam pellets positioned within the plurality of inflatable sections.

21. A compression sleeve, comprising:
a first sheet;
a second sheet attached to said first sheet and defining at least one inflatable section having dimensions in directions generally parallel to the first and second sheets; and at least one conduit arranged in at least one of said inflatable section to maintain separation of the first and second sheets and at least one conduit defines a flow path along at least one of said dimensions of at least one inflatable section for improving fluid flow in and out of at least one inflatable section and inhibiting the formation of one or more fluid pockets during a compression cycle, wherein at least one conduit includes a base member and a plurality of ridges attached to a first surface of the base member, the height of the plurality of ridges is at a minimum at an outer edge of the base member and at a maximum at a central portion of the base member, and further wherein a central rib at the central portion of the base member has a height between 70 mils and 80 mils, thereby defining a low profile compression sleeve.

22. A method for applying pressure to a portion of a patient's body, comprising the steps of:
   attaching a sleeve to the portion of the patient's body, the sleeve including a first sheet, a second sheet attached to said first sheet and defining at least one inflatable section having dimensions in directions generally parallel to the first and second sheets, and at least one conduit arranged in the at least one inflatable section to maintain separation of the first and second sheets;
   connecting a lumen to a source of pressurized fluid, wherein the lumen is attached to the plurality of inflatable sections;
   inflating the sleeve to a pressure, wherein the at least one conduit creates a passage for facilitating the flow of the pressurized fluid, at least one conduit includes a base member and a plurality of ridges attached to a first surface of the base member; and
   deflating the sleeve, wherein a portion of the at least one conduit defines a flow path in one of said dimensions of the at least one inflatable section and the conduit channels pressurized fluid towards the lumen to inhibit the formation of one or more fluid pockets during a compression cycle.

23. The method of applying pressure according to claim 22, wherein the at least one inflatable section is oriented in a direction that is substantially transverse to a longitudinal axis of the limb.

24. The method of applying pressure according to claim 22, wherein the sleeve further comprises a plurality of fasteners comprising hook and loop fastener components adapted for securing the sleeve about a patient's body.

25. The method of applying pressure according to claim 22, wherein the at least one conduit is fastened to one of the first or second sheets.

26. The method of applying pressure according to claim 22, wherein the sleeve is formed from polyvinyl chloride.

27. A compression sleeve comprising a first and a second sheet, the sheets sealed, at a sealing line, to form an inflatable section having dimensions in directions generally parallel to the first and second sheets, the inflatable section having at least one opening for the passageway of a fluid, wherein the inflatable section has at least one structure attached to an inner surface of the first or second sheet, the structure extends approximately from the sealing line inward and substantially along one of the dimensions of the first and second sheets of said inflatable section to maintain separation of the first and second sheets and the at least one structure defines a flow path along at least one of said dimensions, the structure capable of maintaining its shape and channeling the fluid at the interior of the inflatable section toward the passageway used for inflating the area between the first and second sheets, for improving fluid flow in and out of at least one inflatable section and substantially inhibiting the formation of one or more fluid pockets during a compression cycle.

28. A compression sleeve as recited in claim 27, wherein the at least one structure is a conduit.

29. A compression sleeve, comprising:
   a first sheet;
   a second sheet attached to said first sheet and defining at least one inflatable section having dimensions in directions generally parallel to the first and second sheets; and
   wherein the compression sleeve further comprising a plurality of raised surfaces formed at an inner surface of the first or second sheet, the raised surface extend approximately from a sealing line inward and are substantially along one dimension of the first and second sheet, for improving fluid flow in and out of at least one inflatable section.

30. A method for applying pressure to a portion of a patient's body, comprising the steps of:
   attaching a sleeve to the portion of the patient's body, the sleeve including a first sheet, a second sheet attached to said first sheet and defining at least one inflatable section having dimensions in directions generally parallel to the first and second sheets, and at least one conduit arranged in the at least one inflatable section to maintain separation of the first and second sheets;
   connecting a lumen to a source of pressurized fluid, wherein the lumen is attached to the plurality of inflatable sections;
   inflating the sleeve to a pressure, wherein the at least one conduit creates a passage for facilitating the flow of the pressurized fluid, and wherein at least one conduit is attached to an inner surface of the first or second sheet, the conduit extends approximately from the sealing line inward and is substantially along one of the dimensions of the first and second sheets of at least one of said inflatable section; and
   deflating the sleeve, wherein a portion of the at least one conduit defines a flow path in one of said dimensions of the at least one inflatable section and the conduit channels pressurized fluid towards the lumen to inhibit the formation of one or more fluid pockets during a compression cycle.

* * * * *